United States Patent [19]

Schupack et al.

[11] Patent Number: 4,979,390
[45] Date of Patent: Dec. 25, 1990

[54] METHOD AND APPARATUS FOR TESTING RELATIVE PERMEABILITY OF MATERIALS

[76] Inventors: Morris Schupack, 37 Split Rock Rd.; Daniel Schupack, 32 Pine St., No. 21, both of Norwalk, Conn. 06854

[21] Appl. No.: 278,580
[22] Filed: Dec. 1, 1988
[51] Int. Cl.⁵ .............................................. G01M 3/26
[52] U.S. Cl. .............................................. 73/38; 73/40
[58] Field of Search ..................... 73/40, 40.7, 37, 38

[56] References Cited

U.S. PATENT DOCUMENTS

| | | | |
|---|---|---|---|
| 2,108,176 | 2/1938 | Newby | 73/46 |
| 3,184,957 | 5/1965 | Ellis | 73/38 |
| 3,524,342 | 8/1970 | Hobbs | 73/40 |
| 3,861,196 | 1/1975 | Domenighetti | 73/38 |
| 4,002,055 | 1/1977 | Kops | 73/40 |
| 4,052,885 | 10/1977 | Shuck | 73/38 |
| 4,311,037 | 1/1982 | Gotche | 73/38 |
| 4,676,091 | 6/1987 | Schuster | 73/38 |

FOREIGN PATENT DOCUMENTS

| | | | |
|---|---|---|---|
| 3628955 | 3/1988 | Fed. Rep. of Germany | 73/38 |
| 182539 | 10/1983 | Japan | 73/38 |
| 175540 | 8/1986 | Japan | 73/38 |
| 15132 | 1/1988 | Japan | 73/37 |
| 690369 | 10/1979 | U.S.S.R. | 73/38 |
| 759958 | 9/1980 | U.S.S.R. | 73/38 |
| 811110 | 3/1981 | U.S.S.R. | 73/38 |
| 935752 | 6/1982 | U.S.S.R. | 73/38 |
| 1197631 | 7/1970 | United Kingdom | 73/38 |
| 1313093 | 4/1973 | United Kingdom | 73/38 |

OTHER PUBLICATIONS

"Permeability Testing of Site Concrete—A Review of Method and Experience"—The Concrete Society (Nov. 1985).
"Permeability as a Measure of Potential Durability of Concrete" K. Schonlin, H. K. Hiladorf.

Primary Examiner—Hezron E. Williams
Attorney, Agent, or Firm—St. Onge Steward Johnston & Reens

[57] ABSTRACT

An apparatus for testing the relative permeability of materials, particularly concrete structures, comprises a transparent, optically non-distorting head having a gasket, which together with the head defines a head chamber, and which allows the head to be sealed against the structure when a partial vacuum is induced in the head chamber. The decay of the vacuum may be measured, and the rate of decay provides an index of permeability. A liquid may be applied to the surface being tested and will foan to allow identification of cracks and fissures. In alternative embodiment, a fluid is introduced into a secondary chamber defined by a secondary gasket and the head, and the rate of permeation of the fluid into the structure provides a measure of permeability. The vacuum mounted test apparatus allows in-situ testing without requiring the extraction of sample cores from the structure or making invasive attachments to the structure, thus providing a quality control apparatus and method for rapid testing of construction materials.

11 Claims, 4 Drawing Sheets

METHOD AND APPARATUS FOR TESTING RELATIVE PERMEABILITY OF MATERIALS

BACKGROUND OF THE INVENTION

1. Field of the Invention

The present invention relates to methods and an apparatus for in-situ and laboratory testing of the permeability of materials, particularly concrete and masonry structures, including joints in such structures.

2. Background of the Invention

Reinforced and prestressed concrete structures are commonly used in the construction of roadways, bridges, buildings, precast concrete elements and the like. Such concrete structures generally comprise reinforcing steel embedments such as rods, mesh or cables which are enclosed in formed concrete. It has been found that such concrete structures tend to deteriorate, with cracking and spalling of the concrete, when corrosive ions permeate the concrete and cause the reinforcing steel to corrode. Ions such as chlorides are likely to be present where road de-icing salts are used, and in marine environments The chloride ions tend to depassify the alkali components of the concrete, and cause corrosion of the reinforcing steel embedments. The corrosion products of the reinforcing steel have a larger volume than the original steel, and therefore create internal pressures in the concrete structure that cause it to crack and spall.

A related problem is the carbonation of the concrete structure. Carbonation occurs when carbon dioxide and carbon monoxide, from the exhaust of an internal combustion engine or the atmosphere, permeate the concrete and react with the hydrated cement compounds forming calcium carbonate. This tends to neutralize the alkaline environment surrounding the steel embedment making the steel vulnerable to corrosion if moisture and oxygen are available.

Unwanted excessive permeability can occur in all concrete because of poor mix design, e.g. an excessive water content, a lack of fines, or excessive air entrapment; or because of inadequate or inconsistent consolidation; or because of poor finishing of the concrete. In addition to being susceptible to corrosion of the steel embedments, concrete having a high permeability tends to have a lower compressive and tensile strength, and lessened durability and abrasion resistance than concretes of low permeability.

Corrosion problems also arise because of water and chloride ions leakage through joints in the concrete. Leakage through joints, as opposed to permeation through the concrete matrix, can occur in caulked joints such as flexible joints located between slabs of concrete. Leakage can also occur in cold joints, which are joints between portions of a concrete structure which are cast at different times so that the concrete matrix loses continuity. Another location where water leakage problems frequently arise is in anchors for post-tensioning tendons which are typically sealed with a cement mortar patch after post-tensioning.

Sealers, such as silane and siloxane solutions, are often applied to the concrete and masonry to reduce the permeability and leakage of the structures. However sealers tend to erode with time, reducing their effectiveness as barriers to ion intrusion. In addition, a sealer may not be properly or evenly applied to a structure, so that the protection against weathering and ion intrusion varies over the surface of the structure.

Concrete formulations which have low absorption and low permeability have also been developed; however, these formulations are dependent on proper formulation, installation, and curing for their effectiveness, and it is desirable to have quality control mechanism even when these concrete formulations are employed.

In evaluating the permeability characteristics of concrete and masonry, there are three main elements which determine the overall permeability of the structure. These are: (1) leakage through joints and cracks; (2) surface permeability; and (3) matrix permeability. Where there are joints and cracks in the structure, these may be the major sources of liquid and ion penetration into the structure and may dominate any measure of the overall permeability of a structure.

In continuous, undamaged concrete, the surface permeability may be the limiting factor in the overall liquid and ion permeability, for example, in a low density concrete having a properly applied sealer. In other concrete structures, the matrix permeability may be the limiting factor, for example, in a high density concrete with a poor finish.

However, whether the matrix permeability or the surface permeability is the limiting factor in a determination of overall permeability, a measurement of the in-situ surface permeability of a structure using the present invention also gives insight into the matrix permeability and the quality of the concrete or masonry regardless of whether surface or matrix permeability is the limiting factor in permeability.

An evaluation of leakage and permeability of a structure allows a determination the susceptibility to corrosion of the embedments. Generally, surface permeability measurements have involved invasive sampling techniques in which a core or plug sample is removed from the concrete for laboratory testing. The lab testing typically involved placing the core in a tube having a sealing fit, and measuring the absorption of water, the permeation of a gas or liquid due to a pressure gradient, or diffusion of gases or ions due to a concentration gradient, in the core. These operations are typically laborious and expensive, as they require very close tolerances to sealingly fit the core into the tube. In addition, the invasive sampling techniques require repair of the structure when a core is extracted, and the results of such tests usually have little statistical significance since it is impracticable to test many sample cores from a structure, and further, since sample cores of limited area (two to four inches in diameter) are preferably taken in order to avoid excessive structural damage.

Several in-situ tests of permeability have been proposed. U.S. Pat. No. 3,184,957 to Ellis discloses an apparatus which comprises a series of reservoirs which, by the displacement of liquid from one reservoir to another, provide a stream of air or vapor to a dome placed on asphalt paving being tested. The degree of permeability is determined by measuring the time required to displace a fixed volume of liquid or the amount of liquid displaced in a fixed time. In an alternative embodiment, a slight vacuum is provided in the dome by the displacement of liquid.

U.S. Pat. No. 3,861,196 to Domenighetti discloses an apparatus having a central liquid chamber having an open end surrounded by an annular chamber in which a pressurized bladder seals the central chamber. The chambers are placed against the structure to be tested, and a liquid is provided under pressure to the central chamber. The flow rate of the liquid into the central chamber provides a measure of the permeability of the structure.

A report by the Concrete Society entitled "Permeability Testing of Site Concrete—A Review of Methods and Experience" describes the Figg method of determining permeability in which a hypodermic needle is sealed into a hole in a concrete structure and a vacuum provided in the needle. The pressure increase is measured to provide a measure of air permeability of the concrete. The Concrete Society report also describes the initial surface absorption test (ISAT) in which liquid absorption of concrete is tested using a cap which is mechanically attached to the surface of a structure, and into which water is fed from a reservoir. These test apparatii and methods suffer from the need for mechanical attachment such as bolting o gluing of the test equipment to the structure so as to obtain a good seal between the cap and the concrete.

A paper by K. Schonlin and H. K. Hilsdorf entitled "Permeability as a Measure of Potential Durability of Concrete—Development of a Suitable Test Apparatus" (undated) describes a test apparatus for testing permeability of prepared samples of concrete in the laboratory. A concrete disk is cast in an air tight rubber ring. A test apparatus, having a vacuum pump connected to a vacuum chamber located over the concrete disk, measures permeability based on the pressure increase in the vacuum chamber after the vacuum pump is isolated from the vacuum chamber.

It is desirable to provide an in-situ method and apparatus for testing the permeability of the surface of concrete structures which, in addition to testing permeability, allows the tester to identify flaws in the structure which contribute to the permeability, so that appropriate repairs may be made as necessary. In addition, it is desirable to provide a method and apparatus which is easily portable and which may be rapidly set up for testing, without requiring intrusive methods to mount the test equipment. In addition, it is desirable to provide an apparatus and method which easily provides consistent measurements of permeability, allowing the development of a consistent index of permeability with which to compare structures and sealers at any time. It is desirable that such a method and apparatus be adapted to provide a quality control check so that a structure may be tested as it is erected.

SUMMARY OF THE INVENTION

It is an object of the invention to provide an in-situ method and apparatus for testing the permeability of a structure which, in addition to testing permeability, allow the tester to identify flaws in the structure which contribute to the permeability. It is a further object of the invention to provide a method and apparatus which is easily set up and operated without drilling holes or otherwise damaging the structure, and which is portable and which provides consistent measurements of permeability. It is another object of the invention to provide a quality control apparatus and procedure to allow rapid and immediate evaluation of concrete structures even as they are being erected.

A first embodiment of an apparatus for testing permeability of a structure generally comprises a transparent head having primary sealing means for resiliently sealing the head against the structure, the head and primary sealing means defining a head chamber; means for providing a partial vacuum in the head chamber; and means for measuring the vacuum in the head chamber.

The transparent head preferably includes a substantially flat segment through which the structure may be observed. Preferably the transparent head is generally circular, although it may have other shapes, and may, for example, be elongated. In one possible embodiment, the head is shaped for adaption to a curved surface.

The sealing means preferably comprises an elastomeric gasket having a width of about 0.3 inch to about one inch.

The means for measuring the vacuum in the head chamber may comprise a pressure gauge. The means for providing a partial vacuum preferably comprises a vacuum pump; tubing connecting the vacuum pump and the pressure gauge, and connecting the pressure gauge with the head chamber; a valve located in the tubing connecting the vacuum pump and the pressure gauge; and a vacuum relief valve operably connected to the head chamber.

The vacuum measuring means may alternatively comprise means for generating electrical signals representative of the vacuum in the head chamber; and means for displaying an indication of vacuum operatively connected to the vacuum signal generating means. The vacuum measuring means may further comprise means for generating electrical signals representative of time; means operatively connected to the vacuum signal generating means for determining a change in the vacuum signal and providing an electrical signal representative thereof; means operatively connected to the time signal generating means for determining a change in the time signal and providing an electrical signal representative thereof; means operatively connected to the vacuum change determining means and the time change determining means for dividing the vacuum change electrical signal by the time change electrical signal and generating an electrical signal representative of the divided signals; and means operatively connected to the electrical dividing means for electrically displaying an indication of the rate of any decay of the vacuum.

In a second embodiment, the apparatus may further comprise secondary sealing means located inwardly of the primary sealing means for resiliently sealing the head against the structure; a secondary chamber defined by the head and the secondary sealing means; means for providing a fluid to the secondary chamber; means for measuring the quantity of fluid provided to the secondary chamber; and means for measuring the period of time during which the fluid is provided to the secondary chamber. Preferably means for providing the fluid to the secondary chamber under pressure are provided, and preferably the fluid is a penetrating liquid dye.

Preferably the means for providing the fluid to the secondary chamber under pressure comprises a graduated cylinder having its lower end mounted on and connecting with the secondary chamber and having a closed upper end, a fluid injection valve located in the closed upper end, a pressure gauge located to measure the pressure in the graduated cylinder, a pump operably connected to the graduated cylinder for pressurizing the graduated cylinder, a valve located between the secondary chamber and the graduated cylinder to control the flow of fluid into the secondary chamber, and a pressure relief valve operably connected with the secondary chamber.

A method of measuring permeability of the surface of a structure, using either embodiment of the test apparatus, comprises the steps of: positioning the transparent head against the structure; providing a partial vacuum in the head chamber sufficient to hold the head against the structure and to induce a flow of air through the surface of the structure; allowing the vacuum in the head chamber to decay; and measuring the vacuum in the head chamber at intervals of time as it decays.

Preferably, the vacuum in the head chamber is initially induced to a gauge pressure in the range of about 22 to about 26 inches of mercury, and the rate of decay of the vacuum is measured. Most preferably, the vacuum decay is measured to determine the time required for the vacuum in the head chamber to decay from a gauge pressure of 20 inches of mercury to a gauge pressure of 15 inches of mercury.

A method of testing leakage in a test area on a structure, using either embodiment of the test apparatus, comprises the steps of: applying a liquid film to the test area; positioning the transparent head against the test area; providing a partial vacuum in the head chamber sufficient to hold the head against the structure and to induce a flow of air through the surface of the structure; and observing the film through the transparent head to determine the location of fissures in the surface of the structure indicated by foaming of the film. The liquid film used in this method has the ability to foam, and preferably comprises a water soluble foaming agent producing very small bubbles.

A method of testing permeability of a structure, using the second embodiment of the invention, comprises the steps of: positioning the head chamber against the structure; providing a partial vacuum in the head chamber to hold the head against the structure; providing a fluid under pressure to the secondary chamber; measuring the quantity of fluid provided to the secondary chamber at intervals of time. Preferably, the flow rate of the fluid to the secondary chamber is calculated from the measurements of fluid quantity and time. Preferably, the fluid is provided to the secondary chamber at a gauge pressure in the range of about 15 to about 100 pounds per square inch. Preferably, the fluid comprises a penetrating liquid dye or a ph indicator solution.

Other objects, aspects and features of the present invention in addition to those mentioned above will be pointed out in or will be understood from the following detailed description provided in conjunction with the accompanying drawings.

DESCRIPTION OF THE PREFERRED EMBODIMENT

Figure 1:
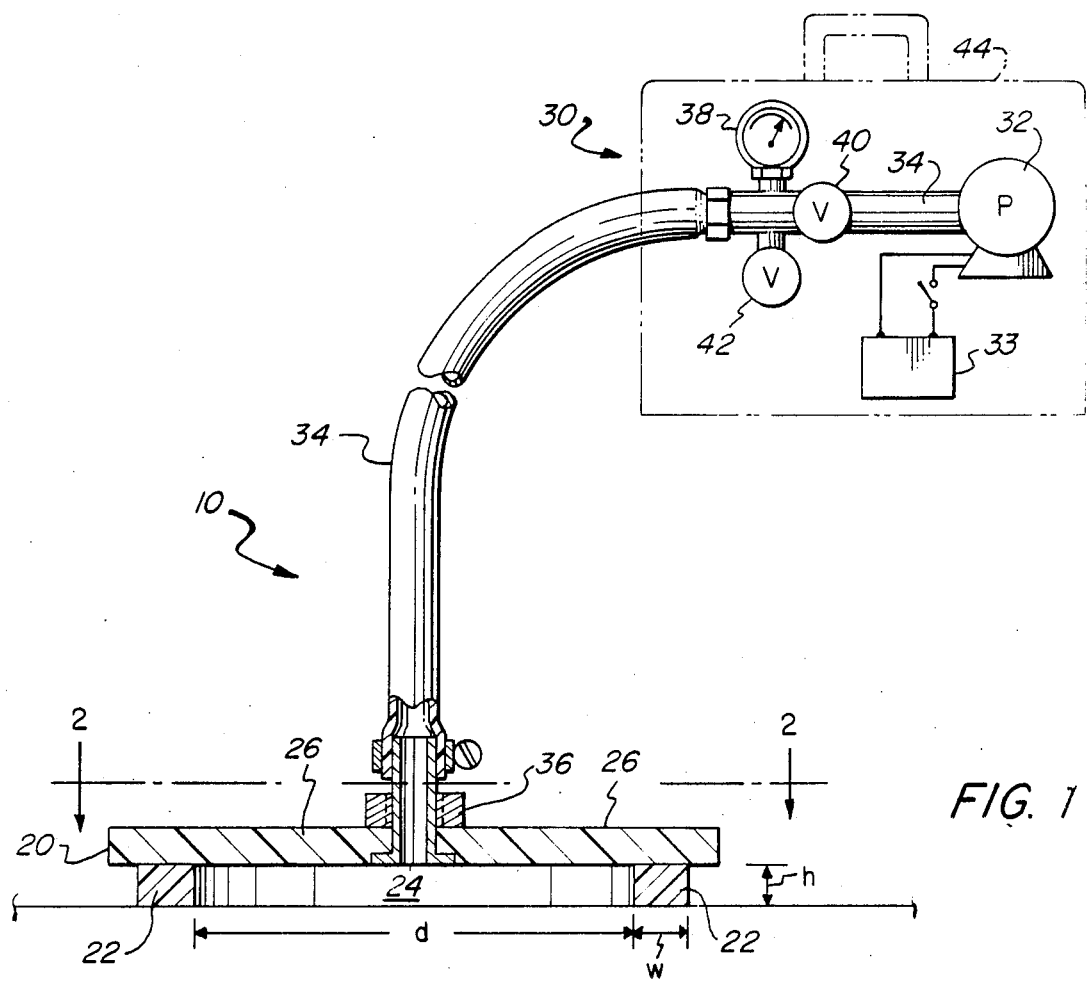
FIG. 1 is a cross-sectional view of a first embodiment of the apparatus of the invention.
Figure 2:
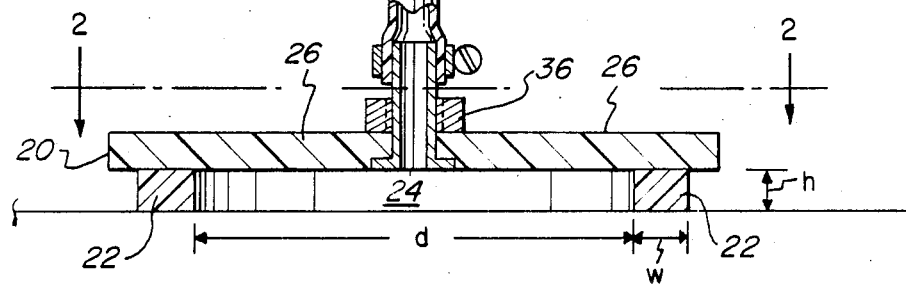
FIG. 2 is a top plan view of the apparatus of FIG. 1, showing flaws detected in a structure.
Figure 2:
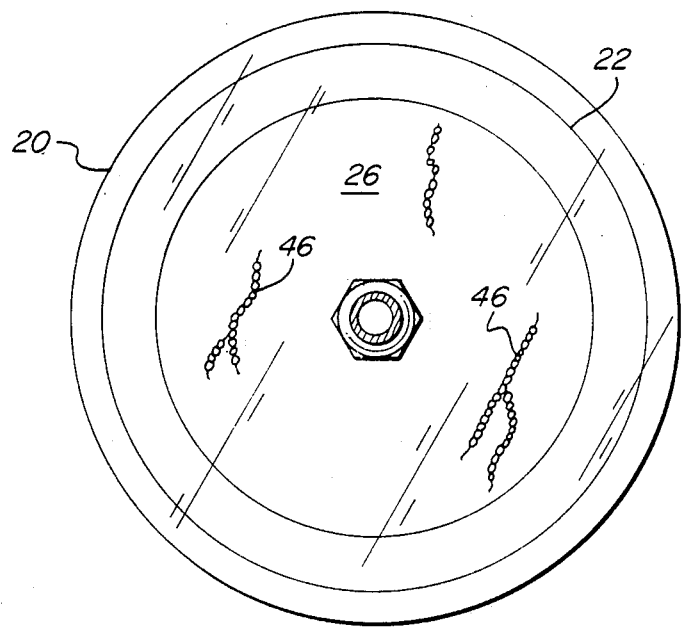

With reference to FIGS. 1 and 2, a first embodiment of the invention comprises an apparatus 10 for testing permeability of a structure. The term permeability as used herein demotes a relative measure of the absorption of a gas or liquid by a solid. The present invention is used to determine a relative measure of permeability using a relatively impervious material such as steel or aluminum plate as a reference. Apparatus 10 comprises a transparent, optically non-distorting head 20, preferably formed from a sheet of a Lexan (a trademark of the General Electric Company for polycarbonate materials). Head 20 has primary resilient sealing means 22, which is preferably an elastomeric gasket made from an elastomer such as silicone or neoprene rubber, located on one face around its perimeter. The head 20 and primary sealing means define a head chamber 24.

Figure 5:
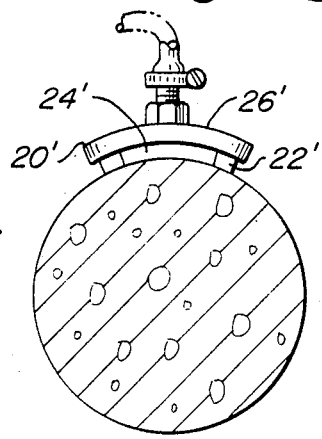
FIG. 5 is a plan view of an elongated embodiment of the test apparatus situated to test a curved structure.
Figure 6:
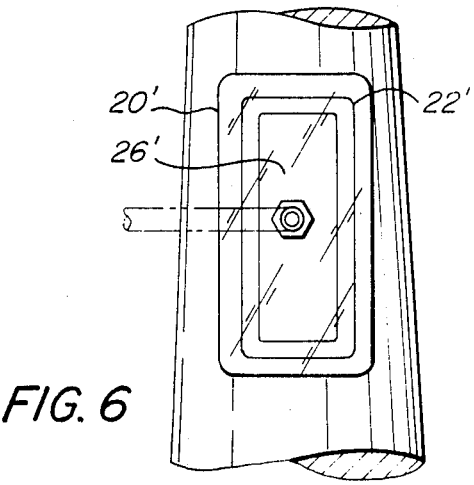
FIG. 6 is a elevation view from the the line 6—6 of FIG. 5.

The head may be shaped and sized to adapt it to the structure to be tested. In the preferred embodiment, head 20 is flat and circular. The diameter d of the head chamber may be varied as desired to test particular structures, but is preferably in the range of about two to twelve inches. The head 20 may be shaped and adapted to particular shapes and structures, and may be generally elongated, as shown as head 20' in FIGS. 5 and 6, so that it may be adapted to test columnar structures such as poles or pilings. A substantially flat, optically non-distorting segment, indicated at 26 in FIGS. 1 and 2 and at 26' in FIGS. 5 and 6, is provided in the head to allow the structure to be observed. If desired, the segment 26 may have optical magnifying properties to permit identification of hairline fissures in the surface of the structure.

The primary sealing means 22 preferably has a thickness h in the range of about three-eighths inch to about one inch, and preferably has a width w in the range of about 0.3 to about one inch. However, if desired, sealing means such as an O-ring of circular, rather than rectangular, cross-section may be used. If desired, the sealing means 22 may comprise a two part gasket, having a first, relatively hard gasket which is adhered to the head 20, and a second, more resilient and deformable gasket which is adhered and sealed to the harder gasket, and which may be replaced for each test. If desired, additional sealants such as silicone or urethane caulking may also be used around the sealing means. Other sealing means may be provided as are known in the art.

The width w of the primary sealing means 22 will be selected depending on the condition of the concrete. For example, it may be necessary to use a wider gasket if there are large imperfections in the surface to be tested which must be bridged, so that any transverse passage of gas between the gasket and the surface of the structure is minimized. It is preferable, however, to use a narrower gasket whenever possible.

Means 30 for providing a partial vacuum in the head chamber 20 are provided. Vacuum providing means 30 preferably comprises vacuum pump 32, which may comprise two ganged piston pumps powered by a battery 33 for field work. A hand powered pump may alternatively be provided. For laboratory work, an A.C. powered pump may be provided. Vacuum pump 32 is connected to the head chamber 24 by tubing 34, most preferably by an air tight quick connect fitting 36.

Means for measuring the vacuum in the head chamber 24 is provided and may comprise a pressure gauge 38 located in tubing 34 between the vacuum pump 32 and the head chamber 24. Valve 40 is preferably provided in tubing 34 between the pump 32 and the pressure gauge 38 to close the connection between the head chamber 24 and pump 32. A vacuum relief valve 42 is operably connected with the head chamber 24, for example, by tubing 34, and allows the vacuum in the head chamber to be vented when desired. For ease of transportation and testing the permeability of structures in situ, the entire partial vacuum providing means and vacuum measuring means may be provided in a suitably sized carrying case 44.

Figure 3:
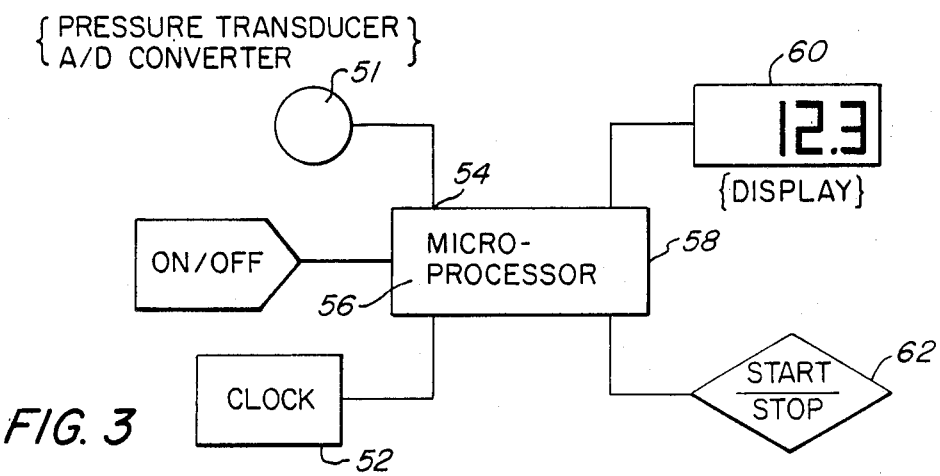
FIG. 3 is a schematic drawing of one embodiment of a vacuum measuring means.

In an alternative embodiment, the means for measuring the vacuum in the head chamber 24 may be designed as a digital sampling and processing circuit, as shown generally at 50 in FIG. 3, and may comprise means 51 for generating electrical signals representative of the vacuum in the head chamber 24, for example, a pressure transducer connected to the head chamber 24, which together with an analog to digital converter provides a digital output; and means operably connected to the vacuum signal generating means for displaying an indication of vacuum, for example, a light emitting diode display. It is also desirable to provide means 52 for generating electrical signals representative of time, for example, a microprocessor clock circuit; means 54 operatively connected to the vacuum signal generating means 51 for determining a change in the vacuum signal and providing an electrical signal representative thereof, for example, a microprocessor circuit; means 56 operatively connected to the time signal generating means 52 for determining a change in the time signal and providing an electrical signal representative thereof, which may be the same microprocessor used to determine change in pressure; means 58 operatively connected to the vacuum change determining means 54 and the time change determining means 56 for dividing the vacuum change electrical signal by the time change electrical signal and generating an electrical signal representative of the divided signals, which may again be the same microprocessor; and means 60 operatively connected to the electrical dividing means for electrically displaying an indication of the rate of any decay of the vacuum.

Preferably, circuit 50 is adapted to provide a default display which is an indication of the vacuum in the head chamber 24, and may be activated to measure and display the rate of the vacuum decay by a switch 62.

A method of measuring the permeability of a structure using the test apparatus described above comprises the steps of: sealingly positioning the transparent head 20 against the structure; providing a partial vacuum in the head chamber 24 sufficient to hold the head 20 against the structure and to induce a flow of air through the surface of the structure; allowing the partial vacuum in the head chamber 24 to decay; and measuring the partial vacuum in the head chamber 24 at intervals of time as it decays. Preferably, the partial vacuum in the head chamber 24 is initially induced to a gauge pressure in the range of about 22 to about 26 inches of mercury, and the vacuum decay is measured to determine the time required for the vacuum in the head chamber to decay from a gauge pressure of 20 inches of mercury to a gauge pressure of 15 inches of mercury. The rate of decay of the vacuum may then be determined by the change in pressure, e.g. from 20 to 15 inches of mercury, divided by the change in time. If the vacuum does not decay to 15 inches of mercury within five minutes, a pressure reading may be taken and the test terminated. Of course other vacuum readings may be taken at other pressures and/or at different time intervals instead of at different pressure intervals, all in accordance with the invention. The rate of decay may be used as an index of permeability useful to compare the relative permeability of structures.

A method of testing the leakage of a test area on a structure using the test apparatus described above comprises the steps of: applying a liquid film to the test area; sealingly positioning the transparent head 20 against the test area; providing a partial vacuum in the head chamber 24 sufficient to hold the head 20 against the structure and to induce a flow of air through the surface of the structure; and observing the film through the transparent head 20 to determine the location of fissures or flaws in the surface of the structure indicated by foaming of the liquid film. Preferably the liquid film is selected to provide relatively small bubbles of foam and most preferably comprises a water soluble foaming agent producing very small bubbles, for example, liquid soap. As shown in FIG. 2, the location of flaws and fissures is easily identified of foam patterns 46 and the intensity of foaming observed through the transparent head 20.

With reference to FIG. 1, the steps of the method may be implemented by closing vacuum relief valve 42 and opening valve 40, starting the vacuum pump 32 and allowing it to operate until the vacuum in the head chamber 24 reaches a maximum, at which time the valve 40 is closed and the pump 32 is shut off. The decay of the vacuum is then observed as described above. When at least two data points have been taken, the vacuum may be vented by opening vacuum relief valve 42, and the head 20 may be removed from the surface of the structure.

This foam bubble test provides a quick test of cold and caulked joints and other test areas to determine the relative leakage through the joint and to identify the location of leaks for subsequent repair.

In order to insure accurate and reproduceable measurements of vacuum decay, it may be necessary to prepare the surface of the structure prior to testing. It is extremely desirable that the head 20 be sealed against the surface during testing. The test surface should be relatively even so that the sealing means 22 will be sealingly fitted against the test surface. It may be necessary to remove protrusions and bumps on the test surface, and fill in any pockets, voids or passages which extend beyond the perimeter of the sealing means 22. In testing joints it may be necessary to seal off the portions of the joint which extend beyond the limits of the sealing means. Polymeric compounds such as plastileen, caulking compounds, wax sealers, gels, and the like may all be used to fill such pockets and voids. Any unintended coatings which could act to seal the test surface, for example, oil patches, should also be removed, for example by scrubbing with a detergent or grinding. A final cleaning of the test surface with a wire brush and removal of any accumulated dust and other particulate matter assures that the test results are not influenced by extraneous factors.

The test surface should be free of standing liquid and have the appearance of surface dryness, since moisture in the pores on the structure will impede air flow and give non-representative test results which will indicate lower degree of permeability than would be obtained with a relatively dry test surface.

Accordingly, when a test surface is being tested for both a measure of permeability and to identify fissures and flaws, it is the better practice to perform the vacuum decay test to measure permeability before identifying fissures using the foam bubble test.

Degradation of the primary sealing means may affect permeation test data. Accordingly, it is important to regularly run calibration tests of the apparatus 10 on a reference surface having known permeability characteristics. If lower maximum pressures or more rapid vacuum decays are observed when calibration tests are run on the reference surface than previously obtained standards, the sealing means should be replaced.

For the first embodiment 10 of the invention, the number of tests to be run depends on the size of the structure, the consistency of construction, the problems being evaluated, the degree of quality control desired, and the findings as testing proceeds. It is desirable to obtain enough readings to understand the overall permeability of the structure. Tests should be made at visible questionable areas (e.g. at visible joints and fissures), and where inconsistent readings are obtained, additional tests should be run.

The present invention is adapted to test many structures, though it has the most immediate utility in the testing of concrete and masonry structures such as tendon anchorage pockets, precast concrete, caulked joints, cold joints, bridges, tanks, dams, roadways, slabs, columns or pilings.

Figure 4:
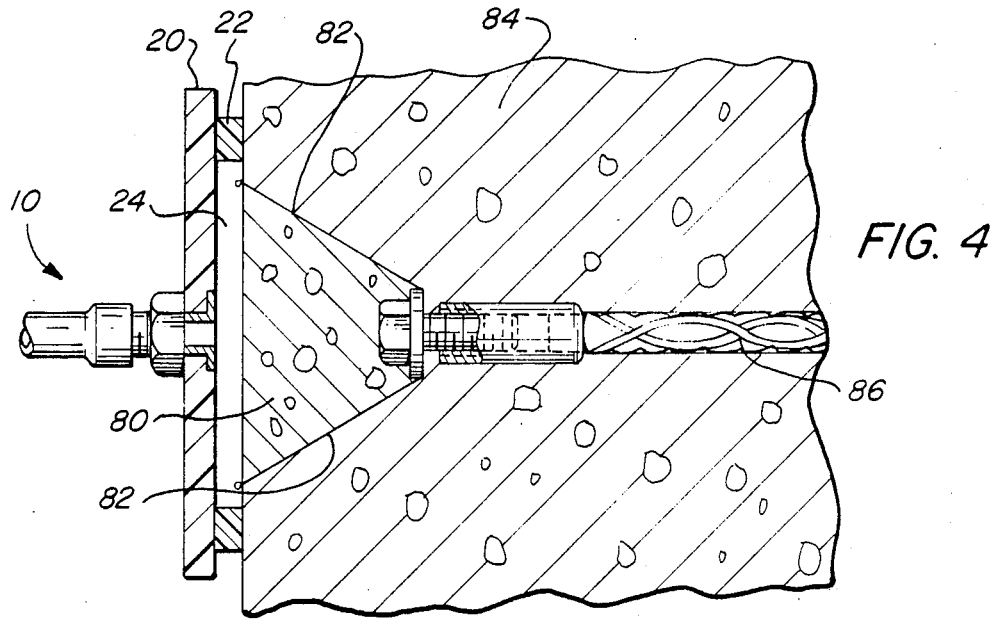
FIG. 4 is a cross-sectional drawing of the apparatus of FIG. 1 situated to test a tendon anchor protection.

The use of the test apparatus 10 in testing the tightness of a post-tensioning tendon anchorage protection is shown in FIG. 4. As can be seen, the head and primary sealing means are preferably sized to encompass the cement mortar patch 80 filling the pocket 82 in the surface of the structure 84. Otherwise each segment of the tendon achorage protection being tested may have to be prepared to seal cracks extending beyond the limits of the sealing means. By using the vacuum decay test in this particular application it is possible to determine whether there is a possibility that water might enter into the structure during construction and promote corrosion of the tendon 86. The foam bubble test may be run to determine the location of leaks to guide repairs.

The vacuum decay test may be performed using apparatus 10 to determine the relative quality of concrete in place in a structure during construction. In the design of concrete structures, the "quality" of the desired concrete is usually defined by specifying materials to be used, a minimum compressive strength (at 28 days) for the concrete, and the slump and air entrainment, within certain tolerances. There are specific control tests for strength, slump and air content which are performed in the field on a limited number of samples of fresh concrete, before it is placed in the structure. Optimally, a concrete mix designed to meet these requirements would allow the concrete contractor to produce, transport, deliver and place into the forms a uniform quality concrete of the desired properties: strength, density, impermeability, durability, etc. However, in the process of mixing, handling and placing concrete, the overall quality of the concrete may be affected and, on occasion, it is desirable to ascertain the relative quality of the concrete in different parts of the structure, particularly in sections of special sensitivity. The procedure for using the first embodiment would first require preparing reference concrete specimens about 12"×12"×6" thick, consolidated and finished similarly to the procedures used on the final structure. A vacuum reading can be taken to obtain a baseline reference for comparisons on the top, finished side, and the formed side and bottom. In lieu of a test specimen a portion of the structure formed from a carefully prepared concrete mix and which is place with special care, and tested for strength, can be used for a reference baseline. The rate of vacuum decay is determined on such test portion on the top finished surface, the side formed surface, and the soffit formed surface. In each case at least three readings of each surface are taken and averaged. These then provide a reference baseline for evaluating other portions of the structure.

If the rate of decline of the vacuum in other portions of the structure is greater by 10% to 20% than the reference, it can be expected that there was a change in the concrete mix, inadequate consolidation or finishing or, that the quality of the concrete has been otherwise compromised. The present invention this provides an important quality control device which allows rapid inspection of concrete in-situ so as to monitor the performance of concrete as soon as it is cured.

In testing older structures, where it may be difficult to determine a baseline index of permeability for evaluation purposes without knowing the components of the concrete mix and the procedures which were used to erect the structure, an estimate of the optimum index of permeability of the structure may be arrived at based on prior testing of similar structures.

Figure 7:
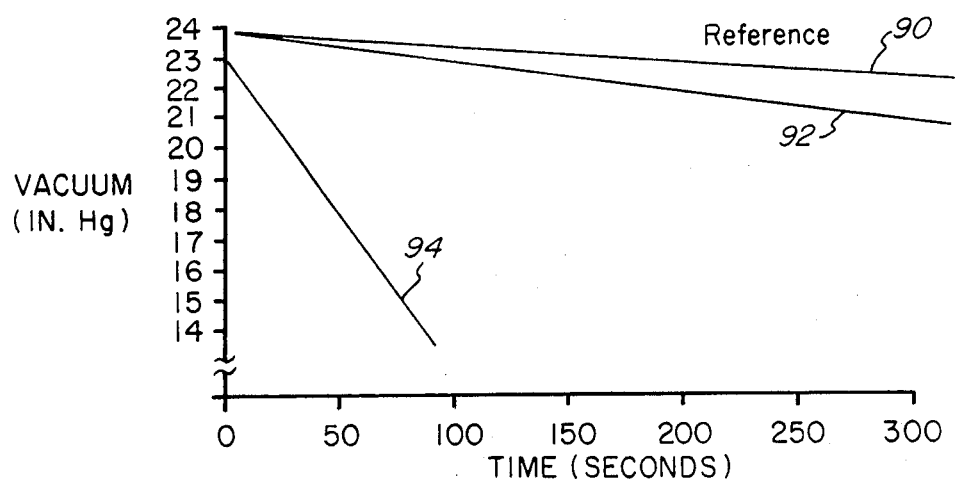
FIG. 7 is a graph showing the decay of the vacuum in the test chamber during the testing of various structures.

The results of comparative testing of several structures using the test apparatus 10 are shown in FIG. 7. In each case, the test head was comprised a flat circle of polycarbonate (Lexan) having a thickness of one-half inch having a test chamber having a diameter d defined by the elastomeric gasket equal to six (6) inches. The elastomeric gasket in each case was $\frac{3}{8}$ inches thick and $\frac{3}{4}$ inches wide and comprised a ring of closed cell neoprene rubber.

The permeability of the test surface of each structure was determined by taking pressure measurements at 0 seconds and 300 seconds. The test samples shown in FIG. 7 were: (1) a reference surface 90 comprised of a sheet of Formica; (2) a top surface 92 of a finished reinforced concrete parking garage having an unblemished surface; and (3) a second top surface 94 from the same concrete parking garage from a area having a highly permeable material. As can be seen, the relatively impermeable formica reference sheet shows little decay in the vacuum; but the rest of the samples show increasing rates of decay due to their higher permeability.

The first embodiment of the invention may also be used as a quality control device, to test the flexural strength of a thin plate. The steps of such a method of testing the flexural strength of a structure comprise sealingly positioning the head 20 against the plate; inducing a partial vacuum in the head chamber 24 to a predetermined level to hold the head 20 against the structure and cause the structure to bend; determining whether the structure has maintained its structural integrity, i.e., if the structure being tested, using a selected length based on the span of test chamber, does not shatter or break, then it has sufficient flexural strength. The quality control application may also comprise a switch activated by contact with the bending structure which shuts off the vacuum and vents the vacuum when the bending of the structure has reached a predetermined point.

Figure 8:
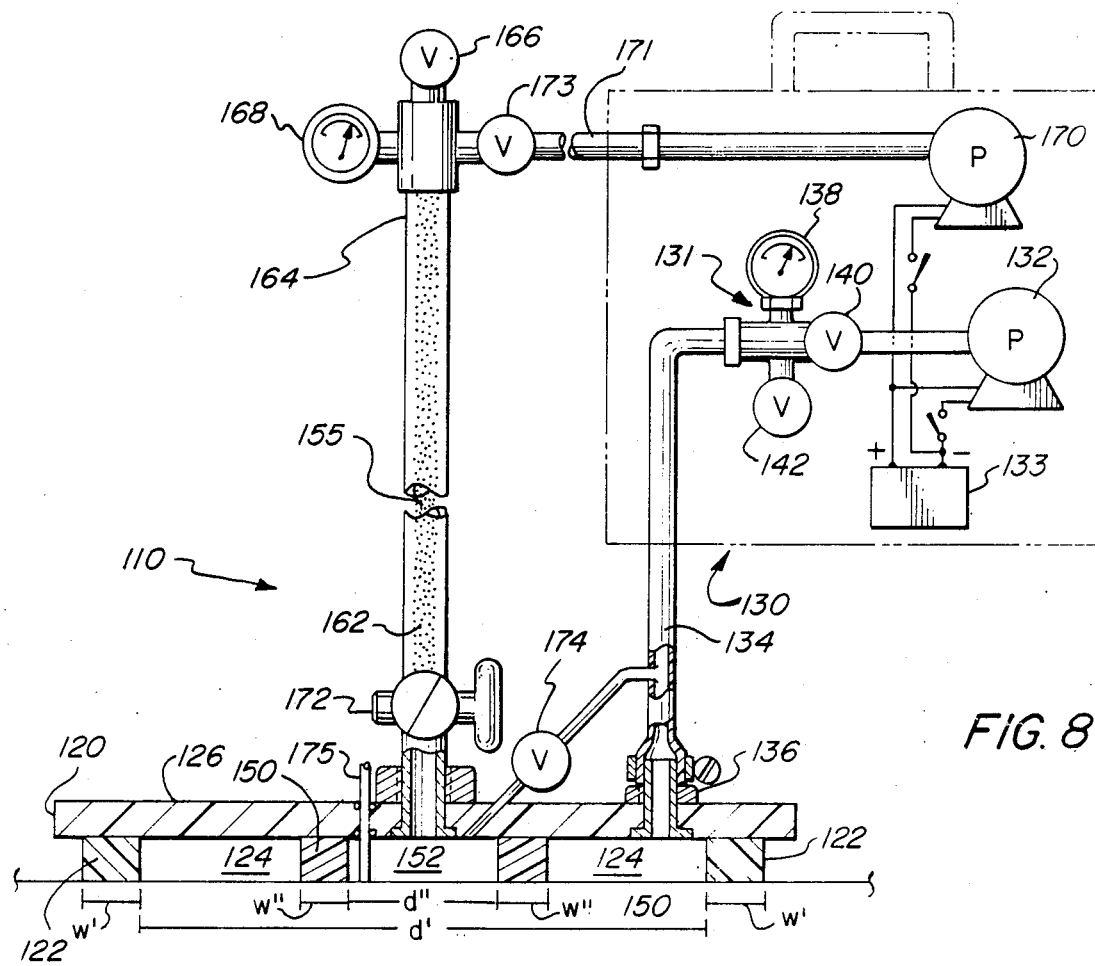
FIG. 8 is a cross-sectional view of a second embodiment of the apparatus of the invention.
Figure 9:
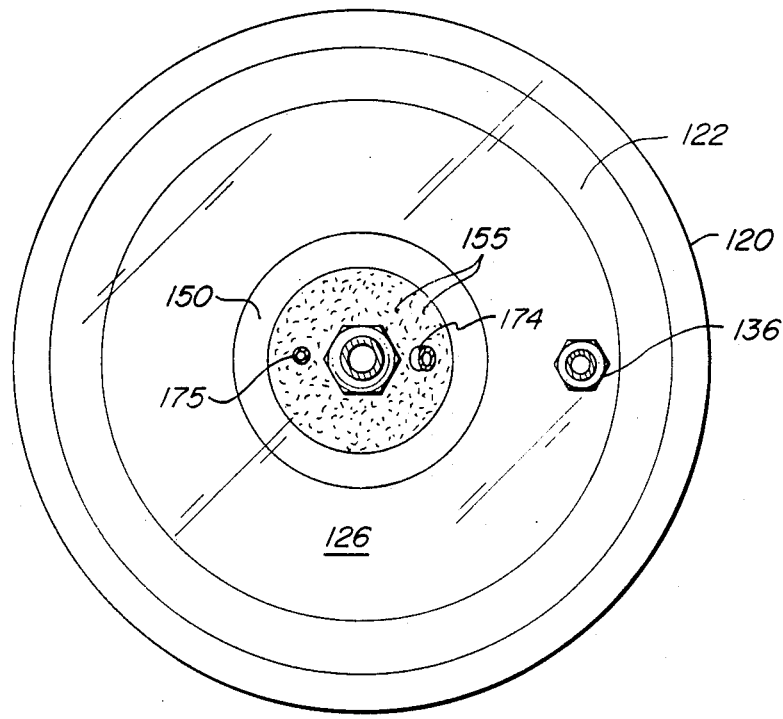
FIG. 9 is a top plan view of the apparatus of FIG. 8.

A second embodiment of the test apparatus is shown as 110 in FIGS. 8 and 9. Apparatus 110 comprises a head 120 having primary means 122 for resiliently sealing head 120 against a structure. Head 120 and primary sealing means 122 define a head chamber 124. Head 120 is preferably transparent and has an optically non-distorting segment 126, and may be formed from Lexan. Head 120 is preferably circular, but may comprise any shape adapted to fit onto the surface of a structure to be tested.

Primary sealing means 122 preferably comprises an elastomeric gasket made of an elastomer such as silicone or neoprene rubber. The primary sealing means 122 preferably has a thickness h' in the range of about three-eighths inch to about one inch, and preferably has a width w' in the range of about 0.3 to about one inch. If desired, the sealing means 122 may comprise a two part gasket, having a first, relatively hard gasket which is adhered to the head 120, and a second, more resilient gasket which is adhered to the harder gasket, and which may be replaced for each test. If desired, the sealing means may be an O-ring of circular cross-section or other gaskets or sealing devices as are known in the art; additional sealers such as caulking may also be employed. The head chamber 124 defined by the primary sealing means 122 preferably has a diameter d' of about ten inches.

Means 130 for providing a partial vacuum in the head chamber 124 are provided, as are means 131 for measuring the vacuum in head chamber 124. The measuring means may comprise a mechanical pressure gauge 138 or an electronic device as previously described. The vacuum providing and measuring means comprise a vacuum pump 132, tubing 134 connecting the vacuum pump 132 and the pressure gauge 138 and connecting the pressure gauge 138 with the head chamber 124, a valve 140 located in the tubing 134 connecting the vacuum pump 132 and the pressure gauge 138, and a vacuum relief valve 142 operably connected with the head chamber. Vacuum pump 132 may comprise two ganged piston pumps powered by a battery 133 for field use. Vacuum pump 132 may however comprise any pump selected to provide a sufficient vacuum as previously described, and preferably even higher vacuums. Tubing 134 is preferably connected to head chamber 124 by a quick connect fitting 136. In order to provide a maximum test area, the vacuum pump 132 may be operably connected a secondary chamber 152 by a valve 174. The second embodiment 110 of the invention may be used as previously described for the first embodiment 10 of the invention, and may be used in the foam bubble test and the vacuum decay test as described in detail above.

Apparatus 110 further comprises secondary sealing means 150 located inwardly of the primary sealing means 122 for resiliently sealing the head against the structure, the head 120 and the secondary sealing means 150 defining a secondary chamber 152; means for providing a fluid 155 in the secondary chamber; means for measuring the quantity of fluid provided to the secondary chamber. Preferably apparatus 110 further comprises means for providing the fluid under pressure to the secondary chamber.

Secondary sealing means 150 preferably comprises an elastomeric gasket having a thickness h" equal to the thickness h' of the primary sealing means 122. Secondary sealing means 150 has a width w" which is preferably about one-half to about one inch. If desired, the secondary sealing means 150 may comprise a two part gasket as described in reference to primary sealing means 122 or a fiber-reinforced gasket. The secondary chamber 152 preferably has a diameter d" which is small in relation to the diameter d' of the primary sealing means 122, and most preferably is equal to about two inches.

In a preferred embodiment, the means for providing the fluid 155 to the secondary chamber 152 and the means for measuring the quantity of fluid provided comprise a graduated cylinder 160 having a lower end 162 mounted on and connecting with the secondary chamber 152 and having a closed upper end 164. A fluid injection valve 166 is located in the closed upper end 164. A pressure gauge 168 is located to measure the pressure in the graduated cylinder 160. The means for providing the fluid under pressure may comprise a battery powered pump 170 for pressurizing the graduated cylinder 160 which is operably connected to the pump by tubing 171 and a valve 173 or it may comprise a tank of pressurized gas. A valve 172 is located between the secondary chamber 152 and the graduated cylinder 160 to control the flow of fluid into the secondary chamber 152. Valve 174 which is operably connected with the secondary chamber 152 to provide a vacuum therein may also be used to release fluid pressure when the test is completed. In order to insure an accurate calculation of the volume of the injected fluid it is necessary to subtract the volume of fluid retained in the secondary chamber 152 after the completion of the test from the total amount provided to the secondary chamber 152. To this end, a measuring ruler 175 may be provided in the head 120 to measure the height of the secondary chamber 152 during testing, so that the volume of fluid retained in the secondary chamber 152 may be calculated based on the height and area of the secondary chamber. Preferably, means for measuring time are also provided to measure the period of liquid injection, and may comprise a stopwatch or other clock mechanisms. For ease of transportation for in-situ testing, the described means for providing a partial vacuum and the pump 170 for pressurizing the fluid 155 may be contained in a carrying case 144.

Preferably, the fluid 155 comprises a liquid, most preferably a water or alcohol based, penetrating, non-staining, liquid dye, or a ph indicator solution such as phenolphthalein solution. Where a ph indicator solution is used, the color of the concrete gives a indication of the level of alkalinity.

The second embodiment of the invention may be used to perform the vacuum decay and foam tests as previously described. In addition, the second embodiment of the invention may be used to perform a fluid injection test described hereafter.

A method of testing the permeability of the surface of a structure, and which is also a test of the absorptivity of the structure, using apparatus 110, comprises: positioning head chamber 124 against a structure; providing a partial vacuum in head chamber 124 to hold head 120 against the structure; providing a fluid to the secondary chamber 152; and measuring the quantity of fluid provided to secondary chamber 152. Preferably the fluid is provided to the secondary chamber 152 under pressure, most preferably at a gauge pressure of about 15 to about 100 pounds per square inch. In pressurizing the fluid, care should be taken that the pressure is not increased beyond the ability of the vacuum in the head chamber 124 to hold the head 120 sealed against the structure. Preferably the time during which fluid is provided to the head chamber 152 is determined. Development of a relative index of fluid permeability based on the fluid injection volume will require that the injection be run for set time periods in order to obtain the most consistent results.

The flow rate of the fluid 155 to the secondary chamber 152 may be calculated by dividing the quantity of fluid injected into the structure by the time period of injection.

Prior to performing the described fluid penetration test, it is advisable to prepare and clean the surface to be tested as described in reference to the vacuum decay test.

Figure 10:
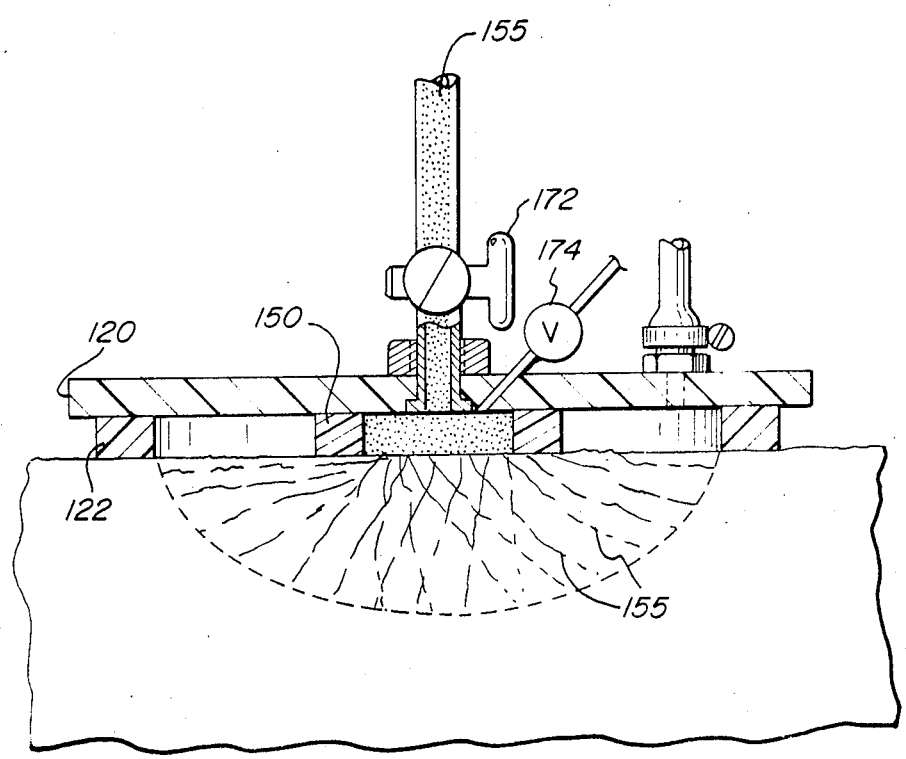
FIG. 10 is a cross-sectional view of the apparatus of FIG. 8 situated to test a structure.

With reference to FIGS. 8-10, the operation of the apparatus 110 to perform the steps of the method of testing involves closing valve 172 and filling the graduated cylinder 160 through valve 166 with a fluid 155. A partial vacuum is then induced in head chamber 124 by closing valve 142, opening valve 140 and activating vacuum pump 132. Valve 173 is then opened and pump 170 is activated to pressurize the fluid 155 to a predetermined pressure, which pressure is indicated on gauge 168. Valve 172 is then opened and the fluid 155 allowed to be injected into the structure, as shown in FIG. 10. The volume of fluid injected and the injection time are measured and the rate of injection determined. When the test is complete, pump 170 is turned off, valves 172 and 173 are closed. Pump 132 is then turned off, and valve 142 is opened to vent the vacuum in head chamber 124, and the head 120 may be removed from the surface of the structure.

The penetrating dye in the method stains the interior of the structure being tested and, if desired, core samples may be removed to investigate the dispersion of the dye within the structure, to provide information on lateral and vertical flow within the structure.

The method described above may be used to test any concrete or masonry structure, and may, for instance, be used to test paved surfaces, bridges and dams.

With the apparatus 110 of the second embodiment of the invention, several fluid penetration tests are performed to determine the overall permeability of the concrete in depth, as opposed to the surface permeability determined by the vacuum decay test. The method of testing using apparatus 110 can be used to determine a reference for further testing on the same structure when the results of the vacuum decay test are inconclusive.

The present invention thus provides a portable, convenient apparatus and method for testing surface permeability of concrete structures, and may be used to evaluate the condition of both sealed and unsealed surfaces. It may be used as a quality control device to evaluate concrete after curing, before it becomes inaccessible under further constructions. It may also be used as part of a periodic monitoring program, in which progressive changes in the condition of the concrete surface may be monitored. It may be used to determine whether a sealer has been properly applied over large areas of a structure by allowing quick comparative testing of the surface of the structure.

The first embodiment of the invention used in the method of the foam test permits the non-destructive identification of small cracks and fissures, and allows an evaluation of the tightness of cold joints, and caulked joints. The method of the vacuum decay test provides a quick, non-invasive test of surface permeability.

The second embodiment of the invention may be used in conjuction with the vacuum decay test, to provide a more precise evaluation of the absorptivity of the concrete than does the vacuum decay test alone, and provides a check on data obtained using the vacuum decay test.

Other adaptions, variations, and modifications of the present invention as would be obvious to a person of ordinary skill in the art may be made, all within the scope of the invention, to allow in-situ testing of the permeability of concrete structures, as well as laboratory or specimen testing.

We claim:

1. Apparatus for testing relative permeability of a structure, comprising:
    a transparent head, having
        an optically non-distorting segment through which said structure may be observed;
        primary means for resiliently sealing said head against said structure, and
        a head chamber defined by said head and said primary sealing means;
    means for providing a partial vacuum in said head chamber;
    means for generating electrical signals representative of said vacuum in said head chamber;
    means operatively connected to said vacuum signal generating means for displaying an indication of vacuum;
    means for generating electrical signals representative of time;
    means operatively connected to said vacuum signal generating means for determining a change in said vacuum signal and providing an electrical signal representative thereof;
    means operatively connected to said time signal generating means for determining a change in said time signal and providing an electrical signal representative thereof;
    means operatively connected to said vacuum change determining means and said time change determining means for dividing said vacuum change electrical signal by said time change electrical signal and generating an electrical signal representative of said divided signals; and
    means operatively connected to said electrical dividing means for electrically displaying an indication of the rate of any decay of said vacuum.

2. Apparatus for testing relative permeability in accordance with claim 1, wherein said transparent head is generally circular.

3. Apparatus for testing permeability in accordance with claim 1, wherein said transparent head is generally elongated.

4. Apparatus for testing relative permeability in accordance with claim 3, wherein said transparent head comprises a curved material for testing curved surfaces.

5. Apparatus for testing relative permeability in accordance with claim 1, wherein said primary sealing means comprises an elastomeric gasket having a width from about 0.3 inch to about one inch.

6. Apparatus for testing relative permeability in accordance with claim 1, wherein said means for providing a partial vacuum comprises:
    a vacuum pump;

tubing connecting said vacuum pump and said pressure gauge, and connecting said pressure gauge with said head chamber;

a valve located in said tubing connecting said vacuum pump and said pressure gauge; and a vacuum relief valve operably connected to said head chamber.

7. Apparatus for testing relative permeability of a structure, comprising:

a transparent head, having primary means for resiliently sealing said head against said structure comprising elastomeric gaskets having a width from about one-half inch to about one inch, and a head chamber defined by said head and said primary sealing means;

an optically non-distorting segment through which said structure may be observed;

means for providing a partial vacuum in said head chamber comprising a vacuum pump, tubing connecting said vacuum pump and said pressure gauge and connecting said pressure gauge with said head chamber, a valve located in said tubing connecting said vacuum pump and said pressure gauge, and a vacuum relief valve operably connected with said head chamber;

secondary sealing means located inwardly of said primary sealing means for resiliently sealing said head against said structure comprising elastomeric gaskets having a width from about one-half inch to about one inch;

a secondary chamber defined by said head and said secondary sealing means;

means for providing a fluid to said secondary chamber under pressure comprising a graduated cylinder having its lower end mounted on and connecting with said secondary chamber and having a closed upper end, a fluid injection valve located in said closed upper end, a pressure gauge located to measure the pressure in said graduated cylinder, a pump operably connected to the graduated cylinder for pressurizing the graduated cylinder, and a valve located between said secondary chamber and said graduated cylinder to control the flow of fluid into said secondary chamber;

means for measuring the quantity of fluid provided to said secondary chamber; and means for measuring the vacuum in said head chamber.

8. Apparatus for testing relative permeability in accordance with claim 7, wherein said transparent head is generally circular.

9. Apparatus for testing relative permeability in accordance with claim 7, wherein said transparent head is generally elongated.

10. Apparatus for testing relative permeability in accordance with claim 7, wherein said fluid comprises a penetrating liquid.

11. Apparatus for testing relative permeability in accordance with claim 10 wherein said penetrating liquid comprises a dye.

* * * * *